(12) United States Patent
Kim et al.

(10) Patent No.: US 12,239,806 B2
(45) Date of Patent: Mar. 4, 2025

(54) PERITONEAL CAVITY-BLADDER CONNECTING CATHETER FOR ASCITES DRAINAGE

(71) Applicant: INJE UNIVERSITY INDUSTRY-ACADEMIC COOPERATION FOUNDATION, Gimhae-si (KR)

(72) Inventors: Il Hwan Kim, Busan (KR); Myeong Ju Kang, Busan (KR); Bong Su Park, Busan (KR); Si Hyung Park, Busan (KR); Yu Jin Lee, Busan (KR); Jin Han Park, Busan (KR); Jae Ha Lee, Busan (KR); Kang Min Park, Busan (KR); Seong Cheol Kim, Busan (KR); Jae Seung Jung, Busan (KR); So Yeong Jung, Busan (KR)

(73) Assignee: INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 815 days.

(21) Appl. No.: 17/289,723

(22) PCT Filed: Oct. 24, 2019

(86) PCT No.: PCT/KR2019/014049
§ 371 (c)(1),
(2) Date: Apr. 28, 2021

(87) PCT Pub. No.: WO2020/091306
PCT Pub. Date: May 7, 2020

(65) Prior Publication Data
US 2022/0001156 A1 Jan. 6, 2022

(30) Foreign Application Priority Data
Oct. 29, 2018 (KR) .................. 10-2018-0129719

(51) Int. Cl.
*A61M 27/00* (2006.01)
*A61M 25/10* (2013.01)

(52) U.S. Cl.
CPC ..... *A61M 27/002* (2013.01); *A61M 25/10182* (2013.11); *A61M 2027/004* (2013.01);
(Continued)

(58) Field of Classification Search
CPC .......... A61M 27/002; A61M 25/10182; A61M 2027/004; A61M 2210/1017; A61M 2210/1085
See application file for complete search history.

(56) References Cited

U.S. PATENT DOCUMENTS 5,370,617 A * 12/1994 Sahota ............... A61M 25/104
604/102.03
5,599,306 A * 2/1997 Klein .................. A61M 25/104
604/509
(Continued)

FOREIGN PATENT DOCUMENTS

EP 2364637 A1 9/2011
KR 10-1481887 B1 1/2015
(Continued)

*Primary Examiner* — Nicholas J. Weiss
*Assistant Examiner* — Peter Daniel Smith
(74) *Attorney, Agent, or Firm* — Bridgeway IP Law Group, PLLC; Sang Ho Lee; Hyun Woo Shin

(57) ABSTRACT

The present disclosure relates to a peritoneal cavity-bladder connecting catheter for ascites drainage. The peritoneal cavity-bladder connecting catheter for ascites drainage includes a peritoneal cavity position part positioned on the side of a peritoneal cavity by passing through a bladder wall located between the peritoneal cavity and a bladder, the peritoneal cavity position part having inlets through which ascites flow into an inner space and being formed as a film that surrounds the inner space, and a bladder position part integrally formed with the peritoneal cavity position part and
(Continued)

positioned on the side of the bladder located on the side of the bladder wall opposite to the peritoneal cavity, the bladder position part having outlets through ascites flowed into the peritoneal cavity position part are discharged to outside, and being configured to form a closed inner space together with the peritoneal cavity position part.

15 Claims, 7 Drawing Sheets

(52) U.S. Cl.
CPC .............. *A61M 2210/1017* (2013.01); *A61M 2210/1085* (2013.01)

(56) References Cited

U.S. PATENT DOCUMENTS

| | | | | |
|---|---|---|---|---|
| 5,662,607 | A * | 9/1997 | Booth | A61M 25/1002 604/104 |
| 6,911,014 | B2 * | 6/2005 | Wentling | A61M 1/285 604/29 |
| 8,388,568 | B2 * | 3/2013 | Lynch | A61M 25/0068 604/9 |
| 10,517,759 | B2 * | 12/2019 | Crimaldi | A61F 9/00781 |
| 2004/0147871 | A1 | 7/2004 | Burnett | |
| 2006/0079845 | A1 * | 4/2006 | Howard | A61M 25/04 604/104 |
| 2013/0006162 | A1 * | 1/2013 | Quintero | A61M 25/04 604/8 |
| 2014/0012180 | A1 | 1/2014 | Levin et al. | |
| 2014/0276347 | A1 * | 9/2014 | Stone | A61M 27/002 604/9 |
| 2017/0072173 | A1 * | 3/2017 | Van Dam | A61B 17/1114 |
| 2018/0039141 | A1 * | 2/2018 | Tseng | G02F 1/133711 |
| 2018/0221632 | A1 | 8/2018 | Scheule et al. | |

FOREIGN PATENT DOCUMENTS

| | | |
|---|---|---|
| KR | 10-1638284 B1 | 7/2016 |
| KR | 10-1671612 B1 | 11/2016 |

* cited by examiner

PERITONEAL CAVITY-BLADDER CONNECTING CATHETER FOR ASCITES DRAINAGE

TECHNICAL FIELD

The present disclosure relates to a peritoneal cavity-bladder connecting catheters for ascites drainage, and more particularly, to a peritoneal cavity-bladder connecting catheter having an improved structure so that ascites within a peritoneal cavity may be discharged in urine through the bladder.

BACKGROUND ART

In liver cirrhosis or peritoneal disseminated diseases (peritoneal carcinomatosis of cancer: when stomach cancer/colon cancer/pancreatic cancer/ovarian cancer is metastasized to the peritoneum), ascites symptoms occur in which water fills the inside of the peritoneal cavity. When ascites symptoms worsen, the patient is accompanied by symptoms such as discomfort, pain, and mobility problems due to abdominal distension.

In this case, as well shown in FIGS. 1 and 2, repetitive ascites punctures (a procedure in which ascites are removed from the abdomen by repeatedly stabbing the abdomen with a needle) are required to improve symptoms. However, because the improvement of the symptoms does not last long, a patient is repeatedly subjected to multiple punctures at intervals of 3 to 5 days (about 2 to 3 liters of ascites are cultured per procedure). This procedure causes a lot of discomfort, such as pain, because the abdomen must be pierced into the peritoneum with a thick needle. As the number of repetitive ascites punctures increases, the intestine may be punctured, causing intestinal perforation, or many complications such as bleeding and infection are accompanied.

There is also a catheter insertion through the intestinal wall (PCD: percutaneous catheter drainage). However, it is difficult to maintain a catheter-mounted state for several days by placing the catheter outside the abdominal wall, and the risk of infection increases as time passes. As the catheter insertion is an external drainage, the patient is limited in movement and feels a lot of discomfort in daily life.

For example, in the case of washing oneself such as taking shower, water may enter the abdomen through a skin part into which the catheter is inserted, and thus the patient feels uncomfortable to wash, and the catheter may often be pulled out during a process of changing clothes.

PRIOR ART DOCUMENTS

KR Patent Registration No. 10-1671612
KR Patent Registration No. 10-1638284

DESCRIPTION OF EMBODIMENTS

Technical Problem

Provided is a peritoneal cavity-bladder connecting catheter for ascites drainage, which enables ascites in the abdominal cavity to be discharged in urine through the bladder, which is an internal organ, via a single procedure, so that pain and discomfort in movement caused by repetitive procedures may be eliminated.

Technical Solution

According to an aspect of the present disclosure, a peritoneal cavity-bladder connecting catheter for ascites drainage includes a peritoneal cavity position part positioned on the side of a peritoneal cavity by penetrating through a bladder wall serving as a basis for separating the peritoneal cavity from a bladder, the peritoneal cavity position part having inlets through which ascites flow into an inner space and being formed as a film that surrounds the inner space, and a bladder position part integrally formed with the peritoneal cavity position part and positioned on the side of the bladder located on the side of the bladder wall opposite to the peritoneal cavity, the bladder position part having outlets through which the ascites flowed into an inside of the peritoneal cavity position part are discharged to outside, and forming a closed inner space together with the peritoneal cavity position part.

The peritoneal cavity-bladder connecting catheter for ascites drainage may further include a balloon support part swollen when the peritoneal cavity position part is positioned on the side of the peritoneal cavity and the bladder position part is positioned on the side of the bladder, to firmly support the peritoneal cavity position part and the bladder position part onto the bladder wall.

Each of the peritoneal cavity position part and the bladder position part may include a passage for injecting air into the balloon support part.

The peritoneal cavity-bladder connecting catheter for ascites drainage may further include a backflow prevention part provided within the inner space to prevent the ascites flowed into the inner space formed by the peritoneal cavity position part and the bladder position part from flowing back into the peritoneal cavity.

Each of the peritoneal cavity position part and the bladder position part may include, at a center thereof, a through hole that is distinguished from the inner space and through which a guide mechanism passes.

The peritoneal cavity-bladder connecting catheter for ascites drainage may further include a backflow prevention check valve provided in the through hole to prevent the ascites from flowing into the peritoneal cavity through the through hole.

Advantageous Effects of Disclosure

According to the peritoneal cavity-bladder connecting catheter for ascites drainage according to an embodiment of the present disclosure having such a structure, a peritoneal cavity position part formed as a film may be guided by a cystoscope and thus positioned within a peritoneal cavity by penetrating through a bladder wall, a bladder position part forming an closed inner space together with the peritoneal cavity position part may remain within the bladder, and the ascites within the peritoneal cavity may be discharged in urine through the bladder through inlets formed in the peritoneal cavity position part and outlets formed in the bladder position part. Accordingly, the peritoneal cavity-bladder connecting catheter for ascites drainage enables repetitive ascites drainages even by a single procedure, and does not require a separate drainage mechanism for ascites drainage and thus not cause discomfort in movement, thereby enabling high-quality medical service provision.

BEST MODE

A peritoneal cavity-bladder connecting catheter for ascites drainage according to an embodiment of the present disclosure will now be described in detail with reference to the accompanying drawings.

Figure 1:
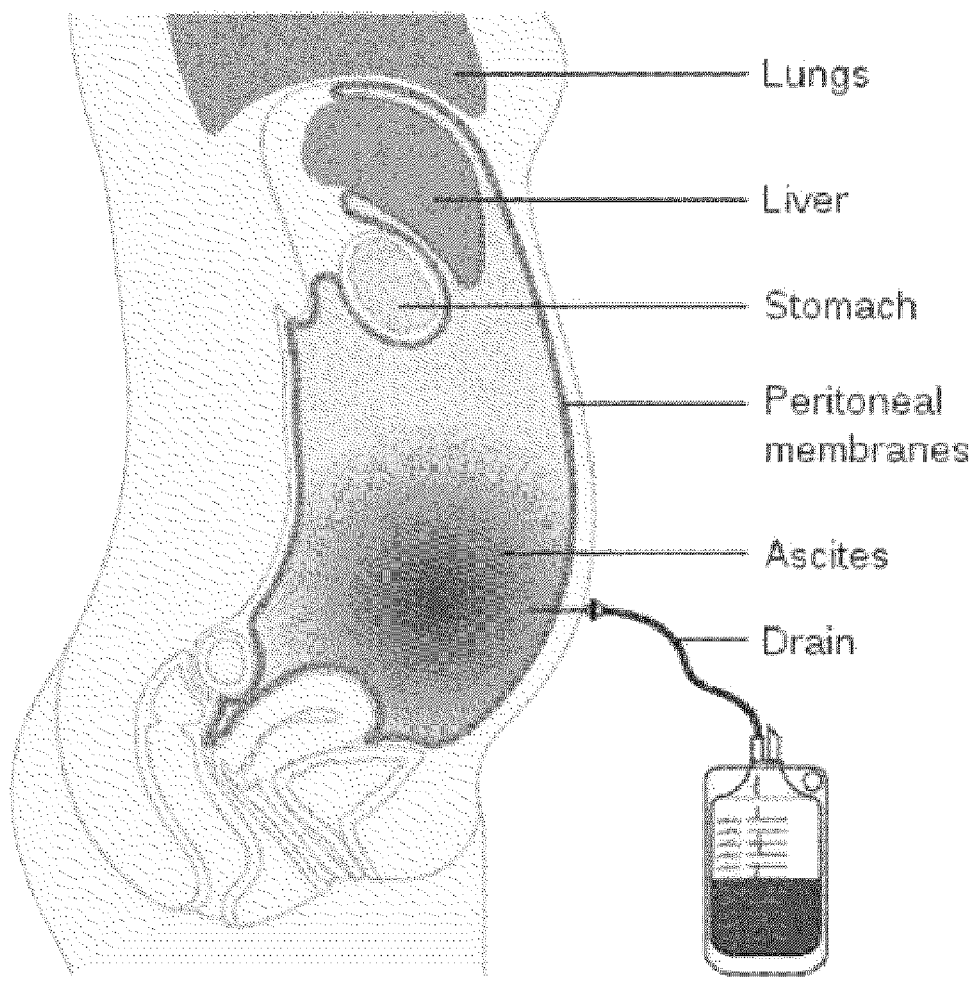
FIGS. 1 and 2 are views for explaining an ascites discharge procedure according to the related art.
Figure 2:
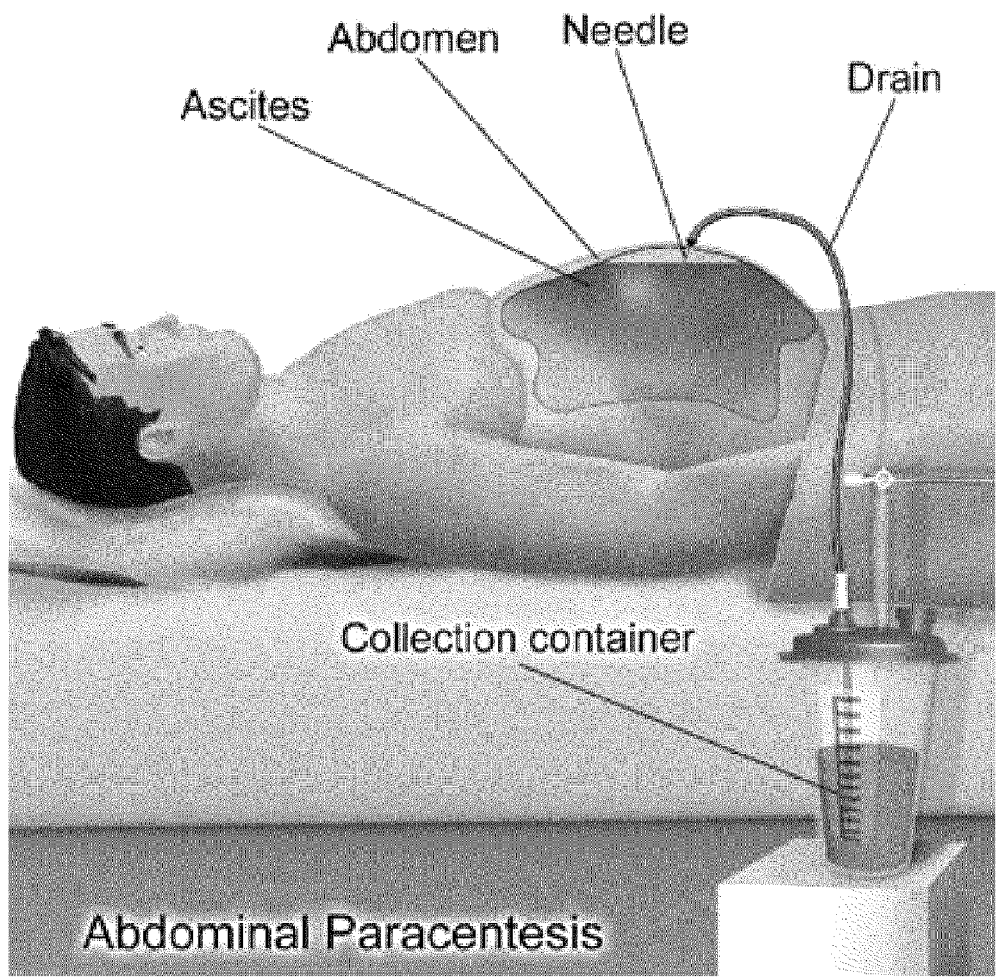
Figure 3:
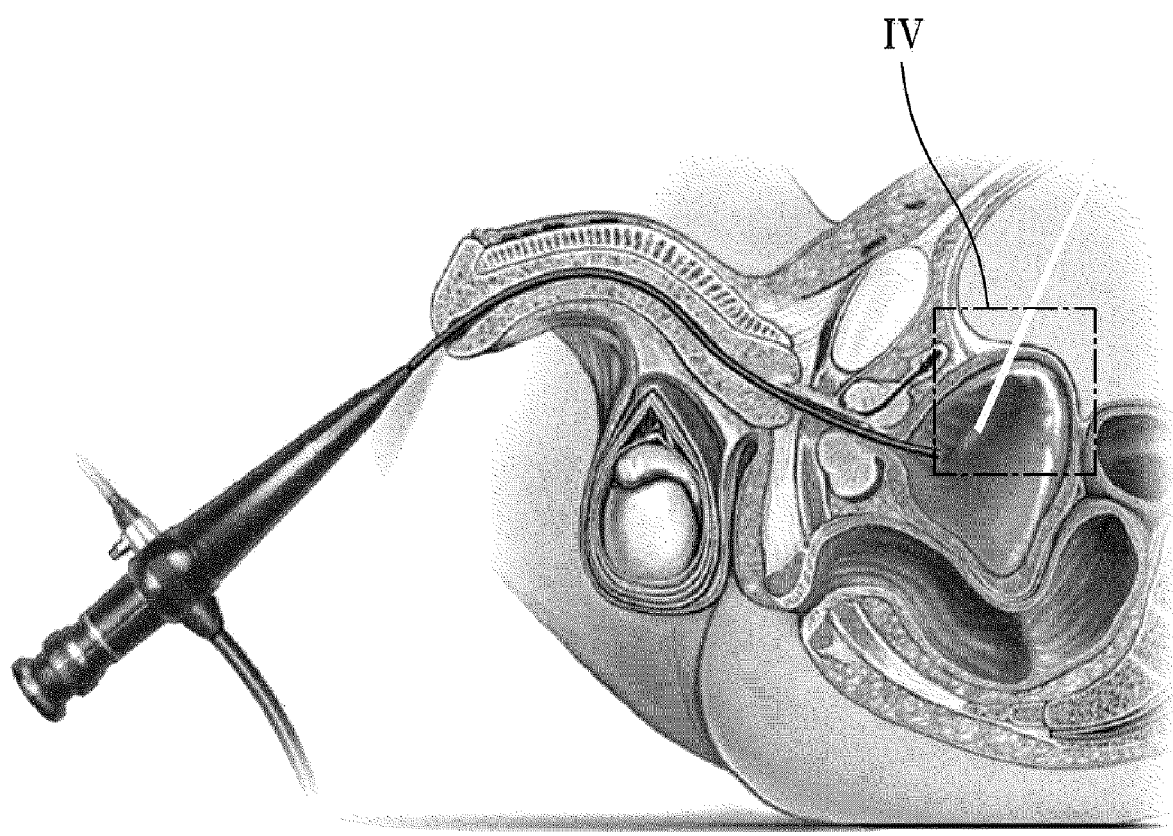
FIG. 3 is a view for explaining a procedure environment of a peritoneal cavity-bladder connecting catheter for ascites drainage according to an embodiment of the present disclosure.
Figure 4:
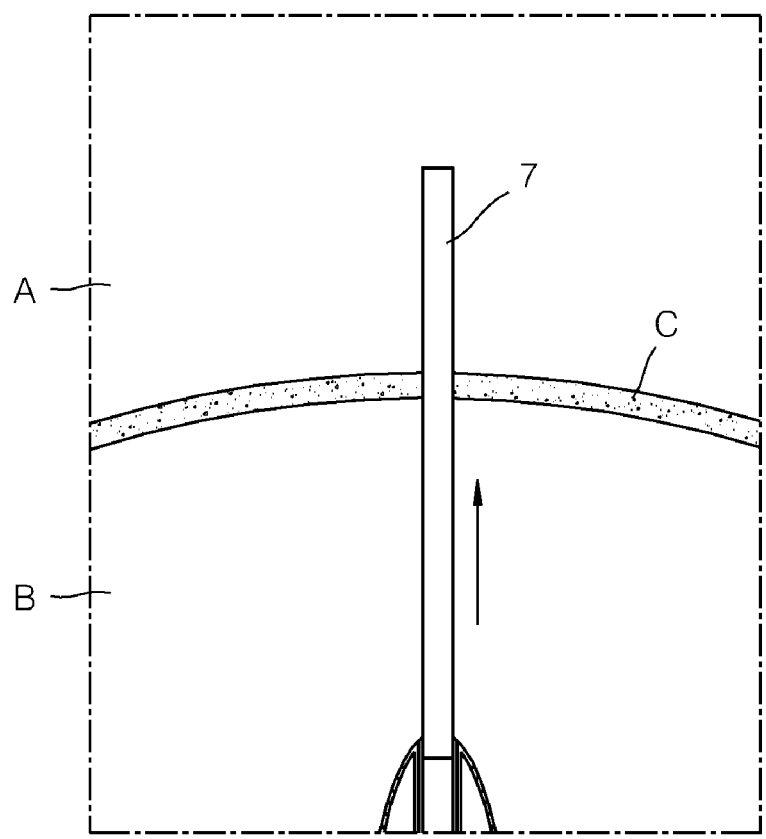
FIG. 4 is an enlarged view of a portion IV of FIG. 3, and illustrates a state where a guide mechanism for guiding an embodiment of the present disclosure to a bladder wall perforates the bladder wall.
Figure 5:
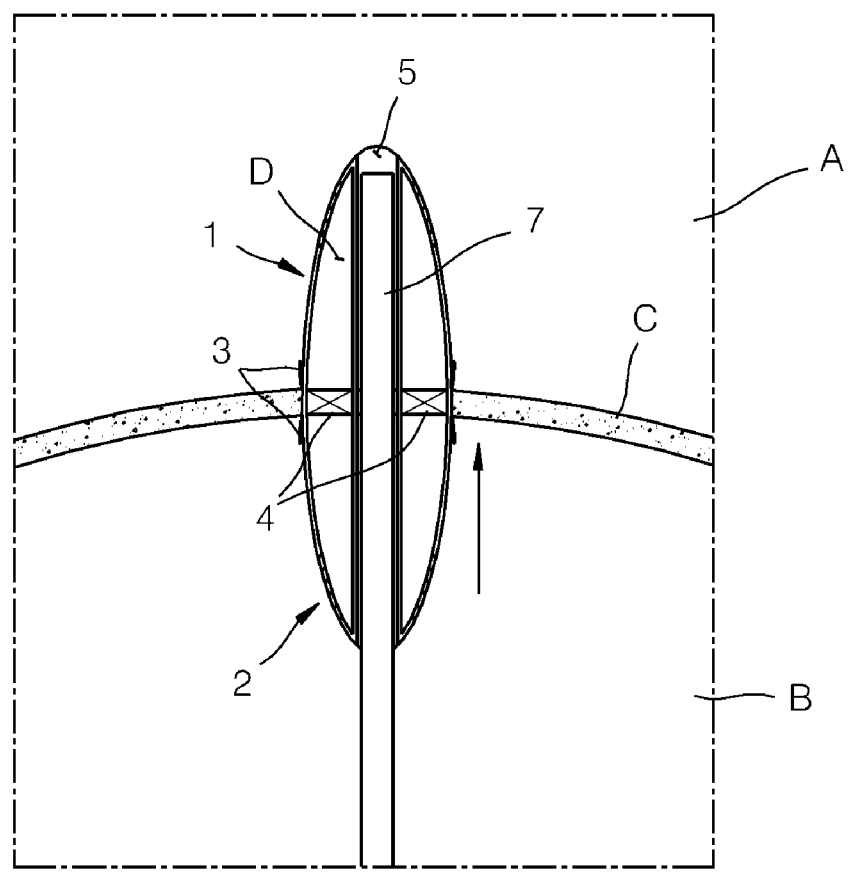
FIG. 5 is a view illustrating a state where the embodiment of the present disclosure is inserted into the perforated portion of the bladder wall.
Figure 6:
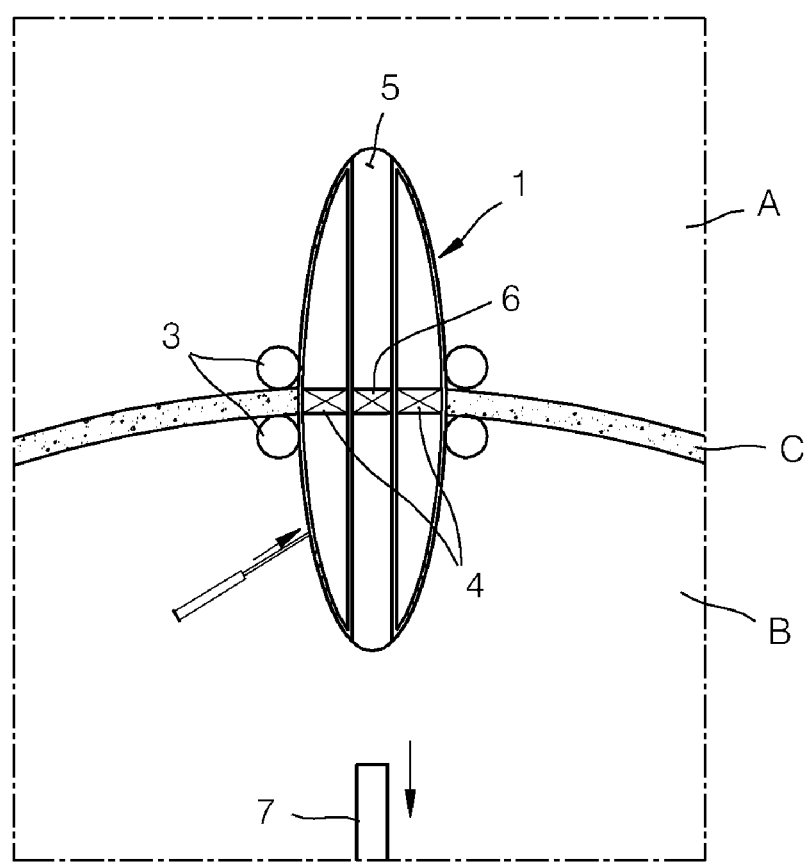
FIG. 6 is a view illustrating a state where the guide mechanism for guiding the embodiment of the present disclosure has been removed and a balloon support part employed in the embodiment of the present disclosure has been expanded.
Figure 7:
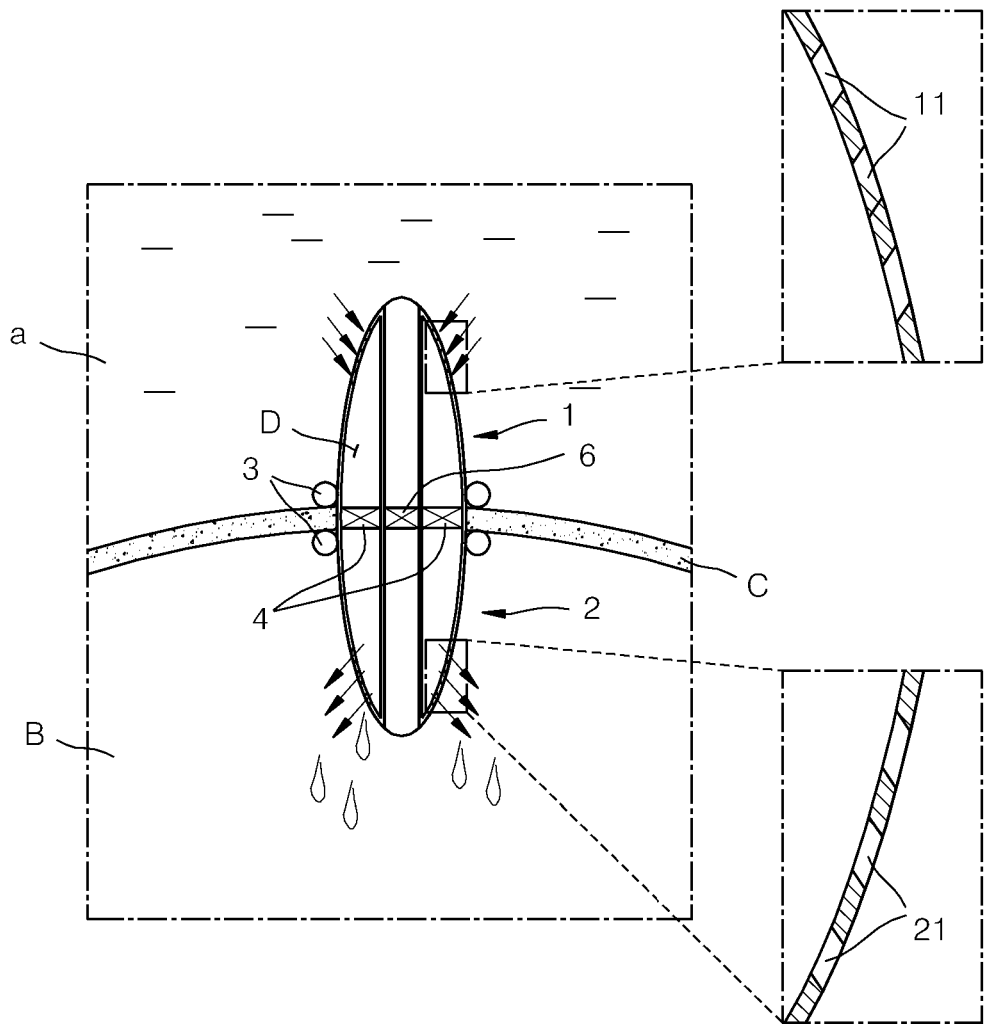
FIG. 7 is a view for explaining a process in which ascites are discharged to a bladder, according to an embodiment of the present disclosure.

FIG. 3 is a view for explaining a procedure environment of a peritoneal cavity-bladder connecting catheter for ascites drainage according to an embodiment of the present disclosure. FIG. 4 is an enlarged view of a portion IV of FIG. 3, and illustrates a state where a guide mechanism for guiding an embodiment of the present disclosure to a bladder wall perforates the bladder wall. FIG. 5 is a view illustrating a state where the embodiment of the present disclosure is inserted into the perforated portion of the bladder wall. FIG. 6 is a view illustrating a state where the guide mechanism for guiding the embodiment of the present disclosure has been removed and a balloon support part employed in the embodiment of the present disclosure has been expanded. FIG. 7 is a view for explaining a process in which ascites are discharged to a bladder, according to an embodiment of the present disclosure.

As shown in FIGS. 5 through 7, the peritoneal cavity-bladder connecting catheter for ascites drainage according to an embodiment of the present disclosure enables the ascites within a peritoneal cavity A to be discharged in urine through a bladder B by connecting the peritoneal cavity A to the bladder B so that fluid is movable, and includes a peritoneal cavity position part 1 and a bladder position part 2.

The peritoneal cavity position part 1 is positioned on the side of the peritoneal cavity A by passing a bladder wall C positioned between the peritoneal cavity A and the bladder B. Inlets 11 through which the ascites flow into an inner space D are formed in the peritoneal cavity position part 1, and the peritoneal cavity position part 1 is formed as a film that surrounds the inner space D.

The bladder wall C separates the peritoneal cavity A from the bladder B, as shown in FIGS. 3 and 4, and is formed of a muscle tissue that may be perforated by a guide mechanism 7 such as a medical needle or wire. As shown in FIG. 3, the present embodiment is able to access up to the bladder wall C through a mirror of the bladder B that enables the inside of the bladder B to be watched and operated.

As show in FIG. 5, the catheter according to the present embodiment includes the peritoneal cavity position part 1 positioned on the side of the peritoneal cavity A by passing a hole perforated in the bladder wall C when being positioned within the bladder B by being guided by the mirror of the bladder B, and the bladder position part 2 positioned in the bladder B existing on the side of the bladder wall C opposite to the peritoneal cavity position part 1.

The peritoneal cavity position part 1 includes the inner space D closed from the outside therein by being formed as a film, and, as shown in FIG. 7, includes a plurality of inlets 11 for communicating the inner space D with the peritoneal cavity A so that fluid is movable.

The bladder position part 2 is integrally formed with the peritoneal cavity position part 1 and positioned on the side of the bladder B located on the side of the bladder wall C opposite to the peritoneal cavity A. As shown in FIG. 7, the bladder position part 2 includes outlets 21 enabling the ascites flowed into the peritoneal cavity position part 1 to be discharged to the outside, and is formed as a film to form the closed inner space D together with the peritoneal cavity position part 1.

The peritoneal cavity position part 1 and the bladder position part 2 may be formed of the same material as that of a medical catheter that is inserted into an organ or tissue of a human body.

The peritoneal cavity-bladder connecting catheter for ascites drainage according to an embodiment of the present disclosure having such a structure is configured such that the peritoneal cavity position part 1 formed as a film may be guided by the mirror of the bladder B and thus positioned within the peritoneal cavity A by penetrating through the bladder wall C, the bladder position part 2 forming the closed inner space D together with the peritoneal cavity position part 1 may remain within the bladder B, and the ascites within the peritoneal cavity A may be discharged in urine through the bladder B through the inlets 11 formed in the peritoneal cavity position part 1 and the outlets 21 formed in the bladder position part 2. Accordingly, the peritoneal cavity-bladder connecting catheter for ascites drainage according to an embodiment of the present disclosure enables repetitive ascites drainage even by a single procedure, and does not require a separate drainage mechanism for ascites drainage and thus not cause discomfort in movement, thereby enabling high-quality medical service provision.

The present embodiment includes a balloon support part 3 for firmly supporting the peritoneal cavity position part 1 and the bladder position part 2 onto the bladder wall C.

In other words, as shown in FIGS. 5 and 6, the balloon support part 3 is swollen like a balloon when the peritoneal cavity position part 1 is positioned on the side of the peritoneal cavity A and the bladder position part 2 is positioned on the side of the bladder B, thereby enabling the peritoneal cavity position part 1 and the bladder position part 2 to be firmly supported by the bladder wall C.

The balloon support part 3 may have a tube structure that is formed to surround respective outer circumferential surfaces of the peritoneal cavity position part 1 and the bladder position part 2.

Each of the peritoneal cavity position part 1 and the bladder position part 2 includes a passage for injecting air into the balloon support part 3.

A process in which the catheter according to the present embodiment is inserted into the bladder wall C and an ascites discharging process will now be described.

In other words, the catheter according to the present embodiment is guided by the guide mechanism 7 of FIG. 4 and is inserted into the hole perforated in the bladder wall C as shown in FIG. 5. Thereafter, as shown in FIG. 6, the balloon support part 3 is expanded due to the air injected thereinto through the passage, and thus the present embodiment is firmly supported by the bladder wall C, and then the guide mechanism 7 is removed from the bladder wall C.

As described above, since the present embodiment is firmly supported by the bladder wall C, even when a punch for repetitive ascites drainages is not performed, the ascites within the peritoneal cavity A are naturally drained to the bladder B through the peritoneal cavity position part 1 and the bladder position part 2 and finally discharged in urine, as shown in FIG. 7.

In the present embodiment having such a structure, because air is injected into the balloon support part 3 through the passage when the peritoneal cavity position part 1 is positioned within the peritoneal cavity A and the bladder position part 2 is positioned within the bladder B, a locking area between the balloon support part 3 swollen due to the air injection and the bladder wall C increases, and thus the peritoneal cavity position part 1 and the bladder position part 2 may be prevented from deviating from their original positions through the hole perforated in the bladder wall C.

A backflow prevention part 4 may be provided in the inner space D formed by the peritoneal cavity position part 1 and the bladder position part 2. In other words, the backflow prevention part 4 prevents the ascites flowed into the inner space D formed by the peritoneal cavity position part 1 and the bladder position part 2 from flowing back into the peritoneal cavity A.

The peritoneal cavity position part 1 and the bladder position part 2 may include, at their centers, a through hole 5 which is distinguished from the inner space D and through which the guide mechanism 7 such as a guide wire or needle passes.

In other words, as shown in FIG. 3, the mirror of the bladder B for guiding the catheter according to the present embodiment is inserted into the urethra for a procedure using the catheter. Such an insertion of the mirror of the bladder B into the urethra enables a procedure within the bladder B. In this state, before the catheter according to the present embodiment is inserted into the mirror of the bladder B, the guide mechanism 7 for perforating the bladder wall C is first made access the bladder wall C through the mirror of the bladder B, as shown in FIG. 4.

Then, the bladder wall C is perforated using the guide mechanism 7, and, when the guide wire is inserted into the through hole 5 of the present embodiment, the present embodiment is moved as shown in FIG. 5 such that a portion of the present embodiment passes through a perforated portion of the bladder wall C and the remaining portion of the present embodiment is positioned within the bladder B. Through this process, the peritoneal cavity A and the bladder B may be connected to each other so that fluid is movable.

As shown in FIGS. 6 and 7, the present embodiment further includes a backflow prevention check valve 6 provided in the through hole 5, and thus may be configured so that the ascites may be prevented from flowing back into the peritoneal cavity A through the through hole 5.

Although various embodiments of the present disclosure have been described above, the present embodiments and the drawings attached to the present specification merely show a part of the technical spirit included in the present disclosure. It will be apparent that modifications and specific embodiments that can be easily inferred by those skilled in the art within the scope of the technical idea are included in the scope of the present disclosure.

The invention claimed is:

1. A peritoneal cavity-bladder catheter, configured to be positioned at a bladder wall, the peritoneal cavity-bladder catheter comprising:

a peritoneal cavity part having a plurality of inlets,
wherein the peritoneal cavity part defines a first space on a side of a peritoneal cavity when configured to be positioned at the bladder wall, and wherein the first space is configured to receive ascites flowed through the plurality of inlets;

a bladder part integrally coupled with the peritoneal cavity part,
wherein the bladder part has a plurality of outlets and defines a second space on a side of a bladder when configured to be positioned at the bladder wall which divides the peritoneal cavity part and the bladder part,
and
wherein the plurality of outlets are configured to discharge the ascites from the second space to outside;

a through-hole penetrating both the peritoneal cavity part and the bladder part, and configured to allow a guide wire to pass there-through,
wherein the through-hole is structurally separated from both the first and the second space formed by the peritoneal cavity part and the bladder part, wherein a first end of the through hole on the side of the peritoneal cavity and a distal end of the peritoneal cavity part are configured to be equally distant to the bladder wall, and a second end of the through hole 2 on the side of the bladder and a distal end of the bladder part are configured to be equally distant to the bladder wall, and
wherein both the peritoneal cavity part and the bladder part have a tapered structure from the bladder wall to the respective distal ends of the peritoneal cavity part and the bladder part; and
wherein when taken in a cross-sectional view perpendicular to a longitudinal direction of both the peritoneal cavity part and the bladder part, a diameter of the cross-sectional view consistently decreases towards the respective distal ends from the bladder wall;

a backflow-prevention part interposed between the peritoneal cavity part and the bladder part, and configured to prevent the ascites flowing from the second space back to the first space;

a backflow-prevention-check valve disposed in the through-hole and configured to prevent the ascites from flowing back into the peritoneal cavity part through the through-hole; and a balloon part positioned on an outer circumferential surface of both the peritoneal cavity part and the bladder part, and configured to elastically support both the peritoneal cavity part and the bladder part.

2. The peritoneal cavity-bladder catheter of claim 1, wherein the first space and the second space have a circumferential surface around the through-hole defining a portion of the first space and the second space being on either lateral side of the through-hole when a longitudinal cross-section of the peritoneal cavity-bladder catheter is taken.

3. The peritoneal cavity-bladder catheter of claim 2, wherein the backflow-prevention part is sandwiched between the portion of the first space and the portion of the second space.

4. The peritoneal cavity-bladder catheter of claim 1, wherein the balloon part has at least a first balloon part and a second balloon part.

5. The peritoneal cavity-bladder catheter of claim 4, the first balloon part is coupled to the outer circumferential surface of the peritoneal cavity part, and the second balloon part is coupled to the outer circumferential surface of the bladder part.

6. The peritoneal cavity-bladder catheter of claim 4, the first balloon part and the second balloon part are distanced apart with a predetermined distance of the bladder wall.

7. The peritoneal cavity-bladder catheter of claim 1, wherein the peritoneal cavity part and the bladder part are facing each other.

8. The peritoneal cavity-bladder catheter of claim 1, wherein the through-hole has a penetration channel extending longitudinally across a center of both the peritoneal cavity part and the bladder part.

9. The peritoneal cavity-bladder catheter of claim 1, wherein the through-hole is configured to accommodate at least one of a medical device or the guide wire.

10. A peritoneal cavity-bladder catheter, configured to be positioned at a bladder wall, the peritoneal cavity-bladder catheter comprising:
   a peritoneal cavity part having a plurality of inlets,
      wherein the peritoneal cavity part defines a first space, and
      wherein the first space is configured to receive ascites flowed through the plurality of inlets;
   a bladder part integrally coupled with the peritoneal cavity part,
      wherein the bladder part has a plurality of outlets and defines a second space, and
      wherein the plurality of outlets are configured to discharge the ascites from the second space to outside;
   a through-hole penetrating both the peritoneal cavity part and a bladder part, and configured to allow a guide wire to pass there-through,
      wherein the through-hole is structurally separated from both the first space and the second space,
      wherein a first end of the through hole on the side of the peritoneal cavity and a distal end of the peritoneal cavity part are configured to be equally distant to the bladder wall, and a second end of the through hole on the side of the bladder and a distal end of the bladder part are configured to be equally distant to the bladder wall, and wherein both the peritoneal cavity part and the bladder part have a tapered structure from the bladder wall to the respective distal ends of the peritoneal cavity part and the bladder part; and
   wherein when taken in a cross-sectional view perpendicular to a longitudinal direction of both the peritoneal cavity part and the bladder part, a diameter of the cross-sectional view consistently decreases towards the respective distal ends from the bladder wall.

11. The peritoneal cavity-bladder catheter of claim 10, further comprising a backflow-prevention part interposed between the peritoneal cavity part and the bladder part; and
   a backflow-prevention-check valve disposed in the through-hole.

12. The peritoneal cavity-bladder catheter of claim 10, further comprising at least one balloon part positioned on an outer circumferential surface of both the peritoneal cavity part and the bladder part.

13. The peritoneal cavity-bladder catheter of claim 10, wherein the first space and the second space have a circumferential surface around the through-hole defining in a portion of the first and the second space being on either lateral side of the through-hole when a longitudinal cross-section of the peritoneal cavity-bladder catheter is taken, and
   wherein a backflow-prevention part is sandwiched between either the portion of the first space and the second space.

14. The peritoneal cavity-bladder catheter of claim 10, wherein the through-hole has a penetration channel extending longitudinally across a center of both the peritoneal cavity part and the bladder part, and
   wherein the through-hole is configured to accommodate at least one of a medical device or the guide wire.

15. The peritoneal cavity-bladder catheter of claim 12, wherein the balloon part has at least a first balloon part and a second balloon part, and the first balloon part coupled to the peritoneal cavity part and the second balloon part coupled to the bladder part are distanced apart with a predetermined distance of the bladder wall.

* * * * *